Jan. 22, 1957 H. H. BLIXEN Plant Pat. 1,556
ROSE PLANT
Filed March 12, 1956
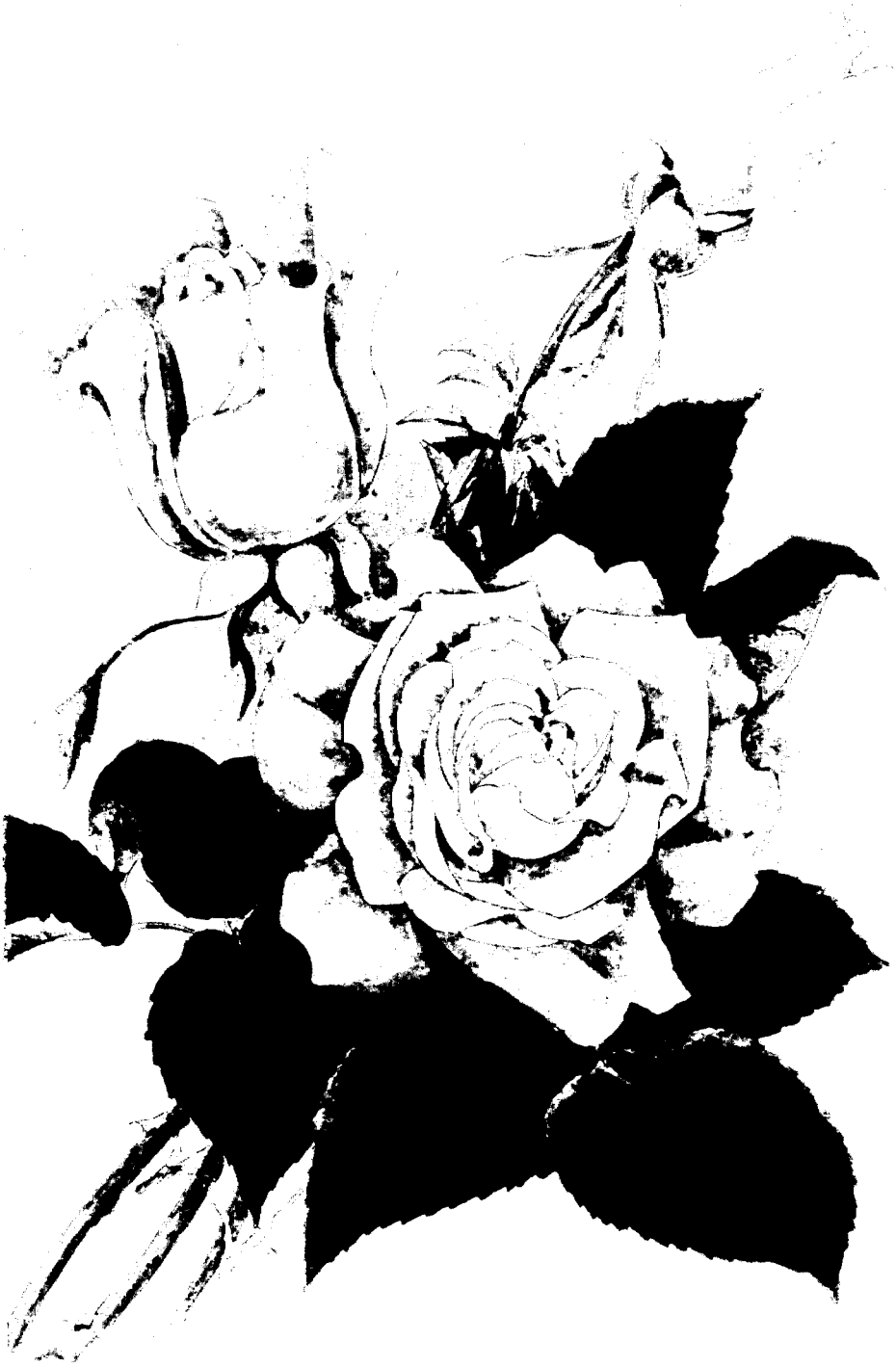
WITNESS
Addison E. Avery
INVENTOR
Harris H. Blixen
by Rummler, Rummler & Snow
ATTYS.

United States Patent Office

Plant Pat. 1,556
Patented Jan. 22, 1957

1,556

ROSE PLANT

Harris H. Blixen, Edwardsville, Ill., assignor to Woodlawn Gardens, Inc., Edwardsville, Ill., a corporation of Illinois Application March 12, 1956, Serial No. 571,110

1 Claim. (Cl. 47—61)

My present discovery, which concerns a new and distinct variety of rose plant, was discovered by me in October, 1951, at my greenhouse at Edwardsville, Illinois, and originated as a sport of "Better Times" (Plant Patent #23). This new variety has been asexually reproduced by me and under my direction at Edwardsville, Illinois, by cuttings, budding and grafting and the new asexually propogated plants show the same distinguishing characteristics as my original discovery.

The primary objects in carrying out this invention were to establish and preserve the depth, brilliance and uniformity of color of the blooms of my new discovery, and to establish a new variety which in many ways is an improvement over the parent plant.

This new variety resembles the parent in many respects but is particularly distinguished from its parent "Better Times," as well as from all other varieties of its class known to me, by the following desirable characteristics:

The uniform and much darker red coloring throughout the blooms; and the retaining of this deep red shade to the base of the petals while opening;

The difference in size and shape of leaf and in stem growth which is stiffer and of harder wood than the parent variety;

The longer length of the leaves which carry more veins than "Better Times" and hence provide a more full and attractive background for the blooms;

The sturdy, firm peduncles;

The greater floriferousness of this new variety over its parent, "Better Times"; and The better keeping of its rich red coloring when stored under refrigeration.

The following is a detailed description in schedule form of my new variety:

Parentage: Sport of "Better Times," Plant Patent No. 23.
Botanic classification: *Rosa odorata.*
Flower:
- *Blooming habit.*—Continuous and profuse.
- *Size.*—4½ inches in diameter.
- *Borne.*—Singly.
- *Shape.*—High center.
- *Petalage.*—Number—30 to 40; form—wavy; color—shading from Old Red to Afghan Red.
- *Discoloration.*—None from bud to full bloom.
- *Texture.*—Leathery.
- *Appearance.*—Velvety. Not affected by wet or hot weather.
- *Fragrance.*—Medium rose.
- *Lasting quality.*—Very good both on plant and as a cut flower.

Bud:
- *Size.*—1½ to 2¼ inches.
- *Form.*—Pointed.
- *Color.*—Copper-Rose.
- *Sepals.*—Stand up over bud and then curl back.

- *Calyx.*—Size—large and long. Aspect—hairy; does not split.
- *Peduncle.*—Length; 12 to 20 mm. Not hairy.

Plant:
- *Form (bush).*—Intermediate.
- *Height.*—Variable.
- *Growth.*—Upright and vigorous. Not branching.

Foliage:
- *Size of leaf.*—15 to 28 cm. by 7 to 17 cm.
- *Texture.*—Smooth, leathery and glossy.
- *Color.*—Upper side, Parsley Green (00962); under side, Leek Green (000858/1) (British C. C. Horticultural Chart).
- *Petioles.*—Length, 1 to 2 inches.
- *Thorns.*—Size, 3 to 12 mm.
- *Color.*—19/1 to 19/3 (British C. C. Horticultural Chart).

Genital organs:
- *Stamens.*—Length, 3 to 5 mm.
  - *Number.*—90 to 120.
  - *Color.*—07 to 07/2 (British C. C. Hort. Chart).
  - *Arranged.*—Singly.
  - *Pollen.*—Fertile. Color, 07 to 07/2 (British C. C. Hort. Chart).
- *Styles.*—Number, 50–80. Length, 1 to 4 mm.
- *Ovaries.*—Number, 5.

Fruit:
- *Fertility.*—Untested.
- *Shape.*—Ovoid.

The color designations of the flower, according to "A Dictionary of Color" by Maerz and Paul, are as follows:

| | Plate | Letter | No. |
|---|---|---|---|
| Back side or reverse of petals "Copper-Rose" | 4 | J | 5 |
| Lightest shade of face of petals "Old Red" | 4 | K | 6 |
| Darker shade of face of petals "Afghan Red" | 4 | L | 6 |

The color designations of the leaves according to British Colour Council Horticultural Chart are as follows: Face of leaf, Parsley Green, 00962 (volume 2, page 193); under side of leaf, Leek Green, 000858/1 (page 197).

This new variety of plant is similar in structure to the parent plant "Better Times" except for the brilliant intensity of its much darker red coloring, the structure of leaf and the harder wood and stiffer stem growth. It has all the good habits of "Better Times": The long compact bud with long sepals hooding the petals until the bud begins to open and furl back; the breadth and depth of the full-blown flower with large petals and compact, high center. The petioles and peduncles are strong and robust.

The profusion of blooms of this new variety of rose plant, combined with their pronounced dark red coloring, the noticeable red veining of the leaves and red-tinted leaflets, the sufficient quantity of large green leaves forming an attractive background for the flowers, give it a distinctive decorative and commercial value.

Having thus disclosed my invention, I claim:

A new and distinct variety of rose plant, substantially as herein shown and described, and characterized as to novelty particularly by the uniform all-over dark red color tonality of the blooms which do not pale when stored in refrigeration, its abundance of large flowers, the large size and pointed shape of the buds, its large green leaves with red veining, its sturdy stiff stems, and its upright vigorous growth.

No references cited.